United States Patent [19]

Raines

[11] Patent Number: 4,631,058
[45] Date of Patent: Dec. 23, 1986

[54] GUARD FOR RIGHT ANGLE WINGED INFUSION NEEDLE

[75] Inventor: Kenneth C. Raines, Bethlehem, Pa.

[73] Assignee: Burron Medical, Inc., Bethlehem, Pa.

[21] Appl. No.: 747,569

[22] Filed: Jun. 24, 1985

[51] Int. Cl.[4] .......................................... A61M 5/325
[52] U.S. Cl. ...................................... 604/263; 604/177
[58] Field of Search ............. 604/263, 192, 197, 198, 604/162, 174, 177

[56] References Cited

U.S. PATENT DOCUMENTS

| | | | |
|---|---|---|---|
| 2,854,976 | 10/1958 | Heydrich | 604/263 |
| 3,658,061 | 4/1972 | Hall | 604/263 |
| 3,822,701 | 7/1974 | Cloyd | 604/192 |
| 3,900,026 | 8/1975 | Wagner | 604/263 |
| 3,904,033 | 9/1975 | Haerr | 604/263 |
| 4,007,740 | 2/1977 | Owen | 604/263 |
| 4,129,128 | 12/1978 | McFarlane | 604/174 |
| 4,139,010 | 2/1979 | Dykstra | 604/263 |
| 4,500,312 | 2/1985 | McFarlane | 604/263 |

Primary Examiner—Dalton L. Truluck
Assistant Examiner—Mario Costantino
Attorney, Agent, or Firm—Shoemaker and Mattare, Ltd.

[57] ABSTRACT

A guard for a right angular winged infusion needle includes a trough like body which receives and protects the needle and a clip portion at one end of the guard extending at right angles to the trough like body snugly grips the wing attachment on the needle to maintain the needle in assembled relationship with the guard.

5 Claims, 7 Drawing Figures

U.S. Patent  Dec. 23, 1986  4,631,058
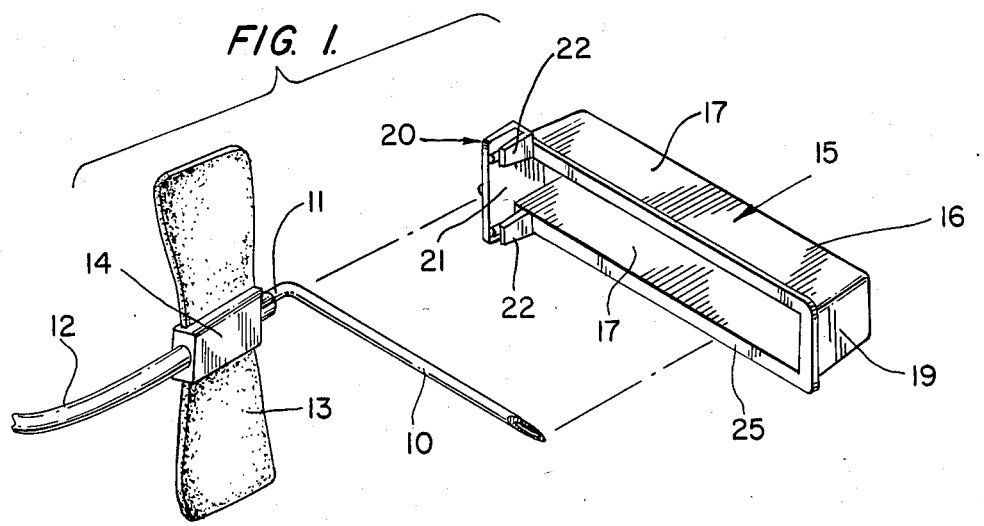
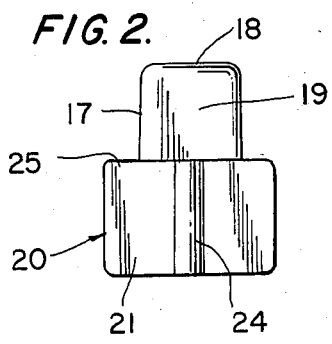 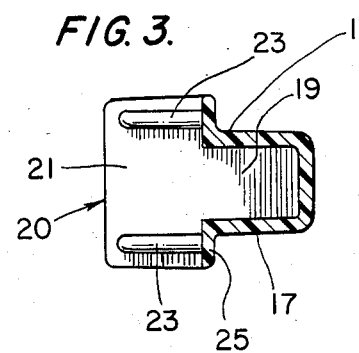 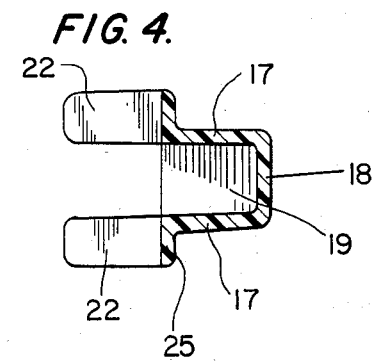
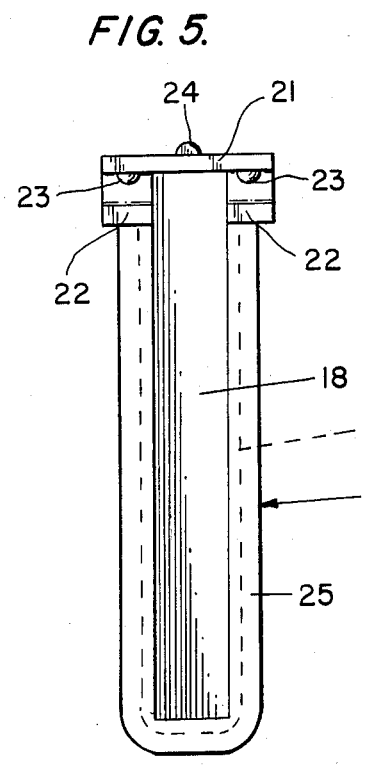 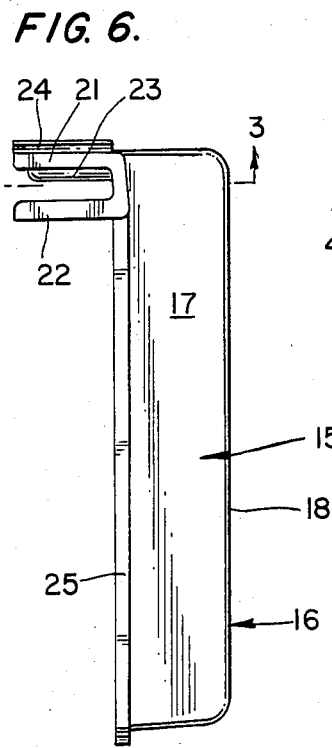 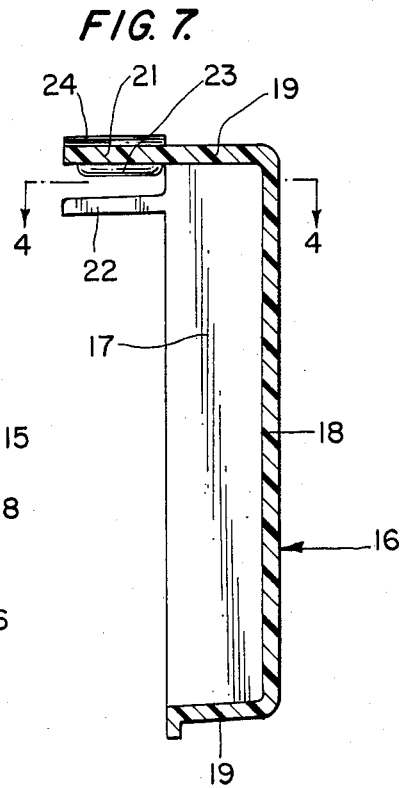

GUARD FOR RIGHT ANGLE WINGED INFUSION NEEDLE

BACKGROUND OF THE INVENTION

Right angular winged infusion needles are becoming ever more popular in the medical field and the present means for protecting such needles has proven to be inadequate. Accordingly, the object of the present invention is to provide a simple and economical guard for right angular winged needles which will adequately protect them during shipment and during periods of non use. More particularly, it is the object of the present invention to provide a one piece guard which can be inexpensively molded from plastics material and applied to the needle quickly and conveniently, and which is also easily removable from the needle and reusable if desired.

The right angular needle guard according to the present invention essentially consists of an elongated trough like body which receives the main shank portion of the needle, and a clip attachment formed integral with the trough like body at one end thereof and projecting from the open side of the trough like body at right angles thereto. The clip attachment embraces the wing of the needle carried by the comparatively short portion thereof which is perpendicular to the main shank portion. The clip attachment maintains the guard releasably secured to the needle in a firm manner.

Other features and advantages of the invention will be apparent to those skilled in the art during the course of the following detailed description.

BRIEF DESCRIPTION OF THE DRAWINGS

FIG. 1 is an exploded perspective view of a right angular winged needle and needle guard according to the present invention.

FIG. 2 is an end elevation of the needle guard.

FIG. 3 is a cross sectional view taken on line 3—3 of FIG. 6.

FIG. 4 is a cross sectional view taken on line 4—4 of FIG. 7.

FIG. 5 is a side elevation of the needle guard.

FIG. 6 is a similar view taken at right angles to FIG. 5.

FIG. 7 is a longitudinal section taken centrally through the needle guard.

DETAILED DESCRIPTION

Referring to the drawings in detail, wherein like numerals designate like parts, a right angular medical infusion needle comprises a main shank portion 10 and a shorter right angular portion 11 connected with an infusion tube 12 and having a somewhat flexible plastics wing attachment 13 fixed thereon, including a generally rectangular hub portion 14 directly secured to the shorter shank portion of the needle.

A guard 15 for the right angular winged needle forms the subject matter of the present invention and is preferably formed as a unit from a suitable moldable plastics material. The guard comprises an elongated substantially rectangular trough like body 16 having substantially parallel side walls 17, a perpendicular longitudinal back wall 18 and a pair of end walls 19 substantially at right angles to the walls 17 and 18. The trough like body 16 of the guard is open along its side opposite to the longitudinal wall 18 so that the shank portion 10 of the infusion needle may be received in the body of the guard for protection.

The guard 15 at one end thereof carries an integral clip attachment 20 projecting away from the open side of the body 16 substantially at right angles thereto. One wall 21 of the clip attachment 20 comprises a continuation of the adjacent end wall 19 and occupies the same plane as this end wall. The wall 21 of the clip attachment is somewhat wider than the adjacent end wall 19 and therefore projects somewhat beyond the two side walls 17 of trough like body 16 as shown in the drawing. The clip attachment 20 further comprises two laterally spaced somewhat resilient fingers 22 spaced from the wall 21 in parallel relationship thereto. On the surface of the wall 21 which opposes the fingers 22 a pair of rounded ribs 23 is provided to enhance the gripping action of the clip attachment 20 with the wing 13 of the right angular needle. A single stiffening rib 24 may also be provided on the other face of the wall 21 midway between the gripping ribs 23 and parallel thereto, as shown. As best shown in FIG. 3, the ribs 23 lie slightly outside of the longitudinal walls 17. As shown in FIG. 4, the resilient fingers 22 are flat and also project outwardly of the side walls 17.

A flat relatively narrow continuous marginal flange 25 is formed on the trough like body 16 at its open side and extends around three sides of the trough like body 16 as shown in FIG. 1. The fingers 22 are integrally joined with the flange 25 near one end of the body 16 as are the portions of the wall 21 which project outwardly of the two side walls 17.

In use, the main shank portion 10 of the infusion needle is received in the elongated trough like body 16 and lies close to its wall 18, substantially in contact therewith. The two sides of the wing 13 are simultaneously received in the clip attachment 20 between its fingers 22 and the opposing gripping ribs 23 on the wall 21. The fingers and ribs snugly grip the wing attachment 13 but allow its easy separation from the guard. The enlarged hub portion 14 of the wing 13 engages between the fingers 22 and between the ribs 23 of the clip attachment 20 and lies upon the interface of the wall 21 when the right angular infusion needle is engaged with the guard 15.

The device is extremely simple and inexpensive, it is convenient to install on and remove from the infusion needle and affords good protection for the latter. Its advantages should be apparent to those skilled in the art.

The flange 25 provides rigidity in the trough like body 16, and the flange may also receive on its outer surface a foil adhesive cover or seal if desired.

It is to be understood that the form of the invention herewith shown and described is to be taken as a preferred example of the same, and that various changes in the shape, size and arrangement of parts may be resorted to, without departing from the spirit of the invention or the scope of the subjoined claims.

I claim:

1. A guard for a right angle winged infusion needle comprising
    an elongated substantially rectangular body including spaced longitudinal side walls, a longitudinal back wall joined to the side walls and a pair of end walls joined to the side and back walls, said body being open along its length away from said back wall, and a clip attachment carried by said body near one end thereof and including a wall substantially contiguous with one end wall of the body and extending outwardly of the opening of the body and further including a laterally spaced pair of somewhat resilient fingers adjacent to the longitudinal side walls of the body and extending outwardly thereof in spaced substantially parallel opposing relationship to the wall of said clip, whereby the shank of a right angle winged infusion needle may be held protectively in said body while a part of the wing of the needle is being held in the clip attachment.

2. A guard for a right angle winged infusion needle as defined in claim 1, and a marginal flange on the side walls and one end wall of the body extending around three sides of the opening of the body and said fingers being fixed on said flange and projecting somewhat laterally outwardly of the longitudinal side walls, and said wall of the clip attachment also projecting somewhat laterally outwardly of said longitudinal side walls and being connected with said flange.

3. A guard for a right angle winged infusion needle as defined in claim 2, and a pair of gripping ribs on the wall of said clip attachment in opposing substantially parallel relationship to said fingers, and a single stiffening rib on the wall of said clip attachment at its surface away from said fingers and substantially midway between and parallel to the gripping ribs and substantially at the transverse center of said body.

4. A guard for a right angle winged infusion needle as defined in claim 3, and said guard being molded as a unit from plastics material.

5. A guard for a right angle winged infusion needle comprising
 an elongated approximately rectangular body which is open along one side and including opposite side longitudinal walls, a back longitudinal wall and a pair of end walls,
 a marginal flange on said body adjacent to its open side and being contiguous with said longitudinal side walls and one end wall and projecting outwardly of such walls approximately perpendicular thereto, and
 a clip attachment on said body substantially at one end thereof and extending outwardly from the open side of the body and away from said back wall, the clip attachment including a clip wall which is contiguous with one end wall of the body and forms substantially a continuation thereof, the clip wall projecting somewhat laterally outwardly of the longitudinal side walls of the body and being joined with said marginal flange and having spaced gripping elements formed on one face thereof, and the clip attachment further including a pair of spaced fingers united with said flange and being in spaced opposing substantially parallel relationship to the clip wall and also being in spaced opposing relationship to the gripping elements and being substantially coextensive lengthwise with the clip wall away from said flange and away from the open side of said body.

* * * * *